US00PP32572P2

(12) United States Plant Patent
Holtmaat

(10) Patent No.: US PP32,572 P2
(45) Date of Patent: Dec. 1, 2020

(54) ***RUDBECKIA* PLANT NAMED 'RUDLU203'**

(50) Latin Name: *Rudbeckia hirta*
Varietal Denomination: RUDLU203

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,138

(22) Filed: Feb. 7, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

*Primary Examiner* — Susan McCormick Ewoldt
(74) *Attorney, Agent, or Firm* — Penny J. Aguirre

(57) ABSTRACT

A new cultivar of *Rudbeckia* plant named 'RUDLU203' that is characterized by its short plant height, its well-branched plant habit, its very floriferous blooming habit, its long flowering period, and its ray florets that are yellow-orange in color that fade lighter towards the tips.

2 Drawing Sheets

Botanical classification: *Rudbeckia hirta.*
Variety denomination: 'RUDLU203'.

CROSS-REFERENCE TO A RELATED APPLICATION

This application is related to a European plant breeders' rights application filed on Sep. 4, 2018, application No. 2018/2268. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Rudbeckia hirta* and will hereafter by referred to by its cultivar name, 'RUDLU203'. The new cultivar is an herbaceous perennial grown for use as a landscape plant.

'RUDLU203' was derived from a breeding program in July of 2016 conducted by the Inventor at a nursery in Zuidwolde, The Netherlands. The objective of the breeding program was to select new cultivars of *Rudbeckia* with floriferous blooming habits and compact plant habits.

'RUDLU203' was selected in July of 2017 by the Inventor from amongst seedlings in a trial field that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January of 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDLU203' as a unique cultivar of *Rudbeckia.*

1. 'RUDLU203' exhibits a short plant height.
2. 'RUDLU203' exhibits a well-branched plant habit.
3. 'RUDLU203' exhibits a long flowering period.
4. 'RUDLU203' exhibits inflorescences with ray florets that are yellow-orange in color that fade lighter towards the tips.

'RUDLU203' can be compared to the *Rudbeckia* cultivars 'Dublin' (not patented), and 'RUDHT37' (U.S. Plant Pat. No. 30,657). 'Dublin' and 'RUDHT37' are both similar to 'RUDLU203' in flower coloration. 'Dublin' differs from 'RUDLU203' in having weaker stems, in commencing bloom later in the flowering season, and in having a less floriferous blooming habit. 'RUDHT37' differs from 'RUDLU203' in having a taller plant height, in commencing bloom later in the flowering season, and in having ray florets that are slightly darker in color.

BRIEF DESCRIPTION OF THE DRAWINGS

The accompanying colored photographs illustrate the overall appearance and distinct characteristics of the new

*Rudbeckia*. The photographs were taken of a 4-month-old plant of 'RUDLU203' as grown outdoors in a 19-cm container in Zuidwolde, The Netherlands.

Figure 1:
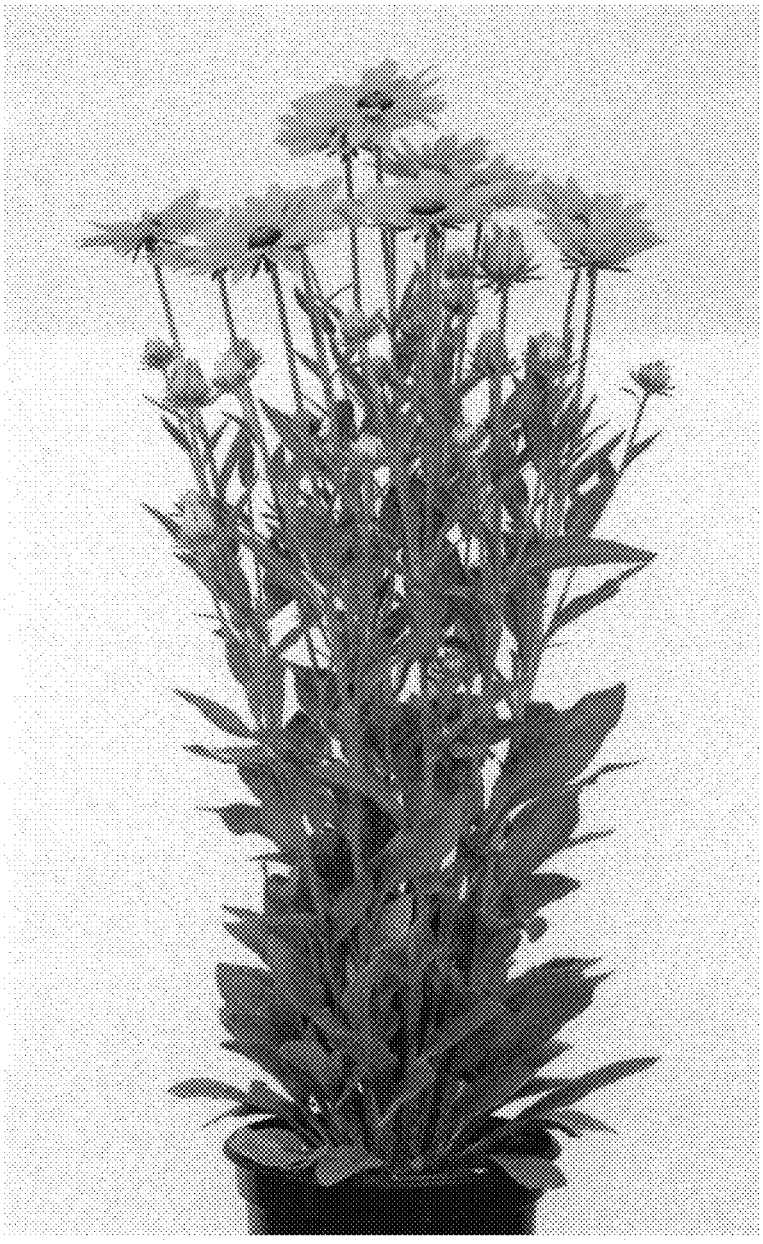

The photograph in FIG. 1 is a side view of 'RUDLU203' in bloom.

Figure 2:
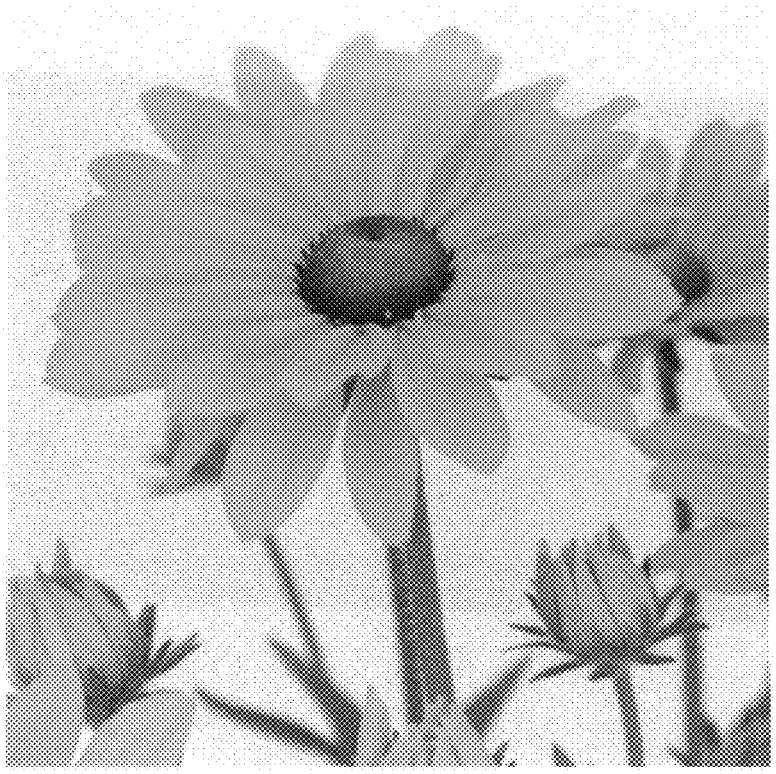

The photograph in FIG. 2 provides a close-up view of an inflorescence of 'RUDLU203'.

Figure 3:
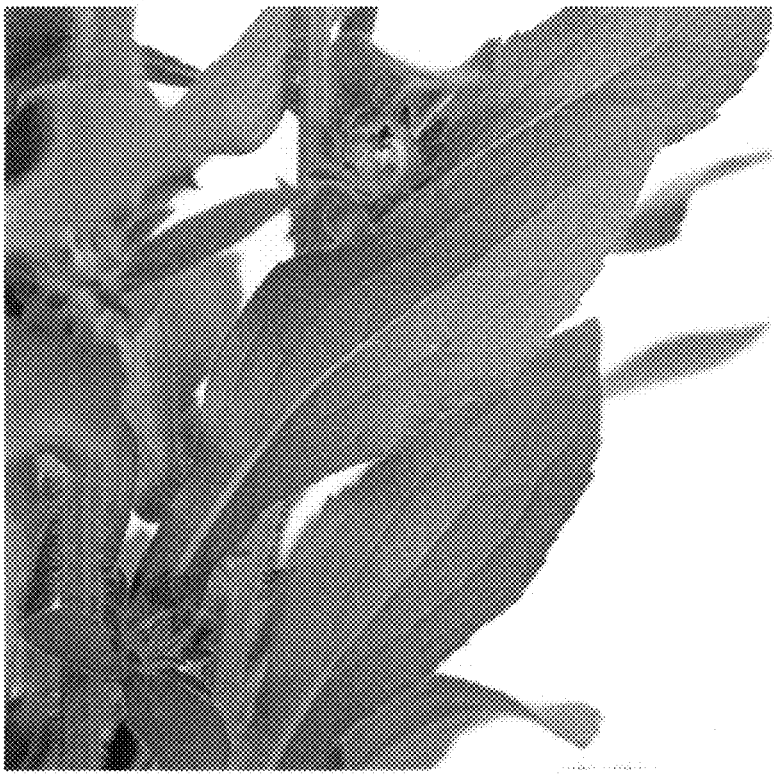

The photograph in FIG. 3 provides a close-up view of the foliage of 'RUDLU203'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDLU203' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in The Netherlands.

*Plant type*.—Perennial.

*Plant habit*.—Broadly upright, compact.

*Plant shape*.—Narrow obovate.

*Height and spread*.—Average of 57.2 cm in height from soil level to top of foliar plane and 69.8 cm in height from soil level to top of floral plane, 35.9 cm in diameter.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Moderate to highly vigorous.

Stem description:

*Shape*.—Moderately angled.

*Stem color*.—Young stems; 144B, mature stems; 144B, angles 143B.

*Stem size*.—An average of 5 mm in diameter and an average of 46.4 cm in height.

*Stem surface*.—Moderately glossy and densely covered with strigose hairs an average of 2 mm in length and close to NN155D in color.

*Stem number*.—Average of 15 main stems, 3 lateral branches per main stem.

*Internode length*.—An average of 4.8 cm in length.

*Stem aspect*.—Main stems; average of 10° to vertical, lateral branches; average of 17.5° to main stems.

*Branching*.—Freely branching from base with lateral stems.

Foliage description:

*Leaf shape*.—Elliptic to obovate.

*Leaf division*.—Simple.

*Leaf base*.—Cuneate.

*Leaf apex*.—Acute.

*Leaf venation*.—Pinnate, color upper surface 147D, color lower surface 146D.

*Leaf margins*.—Coarsely serrate, coarsely slightly undulate.

*Leaf attachment*.—Petiolate.

*Leaf arrangement*.—Alternate.

*Leaf size*.—Average of 10.7 cm in length and 4.3 cm in width.

*Leaf color*.—Young upper surface; 143A, young lower surface; 143B, mature upper surface; 137B and 138A, mature lower surface; 146B.

*Leaf surface*.—Both surfaces rough to the touch, matte and densely pubescent with short strigose hairs; an average of 1.75 mm in length and 156D in color.

*Petioles*.—Average of 5 cm in length, flattened, average diameter at widest point 7 mm and at narrowest point 3 mm, upper surface color; 148D, margins 137B and 138A, lower surface color; 147D, margins 137B, both surfaces slightly glossy and densely covered with strigose hairs; an average of 1.75 mm in length and 156D in color.

Flower description:

*Type*.—Terminal capitulum, consisting of ray florets and disk florets.

*Capitulum number*.—1 per stem, up to 45 per plant.

*Lastingness of inflorescence*.—Average of 2 weeks, persistent.

*Capitulum size*.—Matures to about 2.5 cm in height and 10 cm in diameter, disk size is an average of 2.2 cm in diameter.

*Fragrance*.—None.

*Involucral bracts* (*phyllaries*).—Broadly cuneate base, obtuse to bluntly acute apex, narrow oblong in shape, entire margins, average of 36 arranged in 2 rows, rotate, held in an average of −20°, 1.7 cm in length and 4 mm in width, color; upper surface when fully open 137A, lower surface when fully open 138A, both surfaces slightly glossy and densely covered with strigose hairs; an average of 1.5 mm in length and NN155D in color, margins are moderately to densely covered with strigose hairs 1.5 mm in length and NN155D in color.

*Receptacle*.—Near orbicular in shape, an average of 8 mm in height and 1.1 cm in diameter, 157D in color.

*Buds*.—Globular in shape, immature ray florets pointed upward and curling inward, up to 2.3 cm in length and 3.4 cm in diameter, immature ray florets 153D in color, immature involucral bracts upper surface 137B in color, immature involucral bracts lower surface 138A, surface on involucral bracts and immature ray florets is densely covered with strigose hairs; an average of 1 mm in length, NN156D in color on bracts and 153D in color on immature ray florets.

*Peduncle*.—Strong, straight on top of main flowering stem, average of 12.1 cm in length and 3.5 mm in diameter, color; 144A and axially striped 143B, surface moderately glossy sand densely covered with short strigose hairs; an average of 2 mm in length and NN155D in color.

*Ray florets*.—Average of 21 (varying between 20 and 26), rotate around the disk, oblong in shape, average of 4.5 cm in length and 1.6 cm in width, emarginate to praemorse apex, cuneate base, entire margins, both surfaces are velvety, matte and glabrous, densely covered with very short adpressed hairs, 0.5 mm in length and 15C in color, held near horizontal, color; when opening upper side a color between 17A and 21A, when opening lower side 13A to 13B, changing to 154B and 3B at the base, when fully open upper side 17A, changing to 14A at the tip, when fully open lower side 15B, veins 154C.

*Disk flowers*.—Average about 700 slightly curved and tubular in shape, 16 whorls arranged spirally on a conical receptacle, lower 90% fused into tube, upper 10% free, tubular, about 7 mm in length and 2 mm in width, free lobes have entire margins, apices of free lobes acute and curled backwards, both surfaces glabrous and slightly glossy, color; when opening upper and lower surface 200A, base 157D, when fully open upper and lower surface 155C, tinged 187C, base 155C, spines; none, bracts; 1 per disk floret, flattened, an average of 4 mm in length and 0.8 mm in diameter, oblanceolate in shape, acute apex, narrowly cuneate base, color; apex 200B, mid-section 157A, margined 200B to 200C, base 157A, matte surface and moderately pubescent with hairs; an average of 0.3 mm in length, 200B in color.

Reproductive organs:

*Gynoecium*.—Pistil; 1, 6.5 mm in length, style; 5 mm in length, color; top 200A, mid-section 155C, tinged 187C, base 155C, stigma; cleft, decurrent, 5 mm in diameter, 200A in color, ovary; 156D in color.

*Androecium*.—Stamens; 5, filaments; 2 mm in length, 155B in color, anther; narrow oblong in shape, 2.5 mm in length, 0.5 mm in width, 200A in color, pollen; moderate in quantity and 17A in color.

*Fruit/seed*.—None observed.

It is claimed:

1. A new and distinct cultivar of *Rudbeckia* plant named 'RUDLU203' substantially as herein illustrated and described.

* * * * *